United States Patent [19]

McCowan

[11] 4,180,077
[45] Dec. 25, 1979

[54] DEVICE FOR TREATING SWOLLEN SURFACE AREAS ON HORSES AND THE LIKE

[76] Inventor: Lida L. McCowan, 8370 N. 43rd St., Augusta, Mich. 49012

[21] Appl. No.: 825,309

[22] Filed: Aug. 17, 1977

[51] Int. Cl.² ............................................. A61F 7/00
[52] U.S. Cl. .................................... 128/402; 128/258
[58] Field of Search .................. 128/400, 402, 65, 66, 128/258, 254

[56] References Cited
U.S. PATENT DOCUMENTS

| | | | |
|---|---|---|---|
| 701,521 | 6/1902 | Studley | 128/66 X |
| 998,804 | 7/1911 | Salisbury | 128/65 X |
| 3,075,517 | 1/1963 | Morehead | 128/402 X |
| 3,905,367 | 9/1975 | Dapcich | 128/400 X |

*Primary Examiner*—John D. Yasko
*Attorney, Agent, or Firm*—Haven E. Simmons; James C. Nemmers

[57] ABSTRACT

A device for treating swollen surface areas on horses and the like consists of an elongated envelope-like receptacle which is supplied with water. One side of the receptacle is equipped with water outlets and faces the affected area for discharge thereon, the device being supported in position from the body of the animal itself.

4 Claims, 4 Drawing Figures

DEVICE FOR TREATING SWOLLEN SURFACE AREAS ON HORSES AND THE LIKE

BACKGROUND OF THE INVENTION

Often a swollen or similar area on the body of a larger animal such as a horse is treated by running cold water or other liquid over the affected area. This is a laborious and tiring procedure ordinarily because, typically, the treatment lasts thirty to forty minutes and, since a hose is usually employed, both it and the horse must be held during that time. Indeed, sometimes the treatment must be repeated more than once a day. So far as is known, the only available device that helps out in these circumstances are large "boots" into which the horse's legs are placed and through which is run cold water. But these are at best only partial solutions since they can be used only up to slightly above the knees and thus cannot be used to treat any other areas. Moreover, many horses balk and refuse to allow themselves to be placed in the "boots", or unless tied or securely held, move about, knocking the "boots" off or otherwise impairing their function. The chief object of the present invention, therefore, is a device which avoids the foregoing limitations and problems when treating swollen areas on horses and the like.

SUMMARY OF THE INVENTION

Essentially, the present invention employs an elongated, envelope-like receptacle of flexible material having two opposite exterior faces. A water inlet for attaching a hose is located on one face while the other is provided with a number of water outlets therealong. One side edge of the receptacle is fitted with grommets or the like to attach a strap by which the device can be supported at various places upon the body of the horse so that the water outlets discharge directly upon the affected area. Velcro fasteners are included so that the device can also be wrapped around a leg. Hence by using one or more of the devices any area of the horse's body can be treated as well as the legs. Since the device is attached to and supported by the horse's body itself, not only is there no need constantly to attend or hold the animal during treatment, but also he can move about during that time.

DETAILED DESCRIPTION OF THE PREFERRED EMBODIMENT

Figure 1:
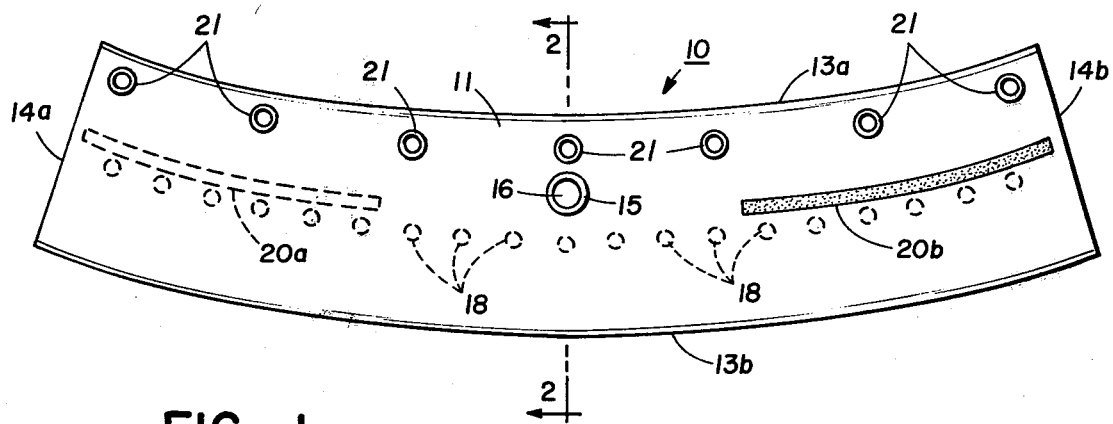
FIG. 1 is a plan view of the device in flat but with the supporting strap omitted.
Figure 2:
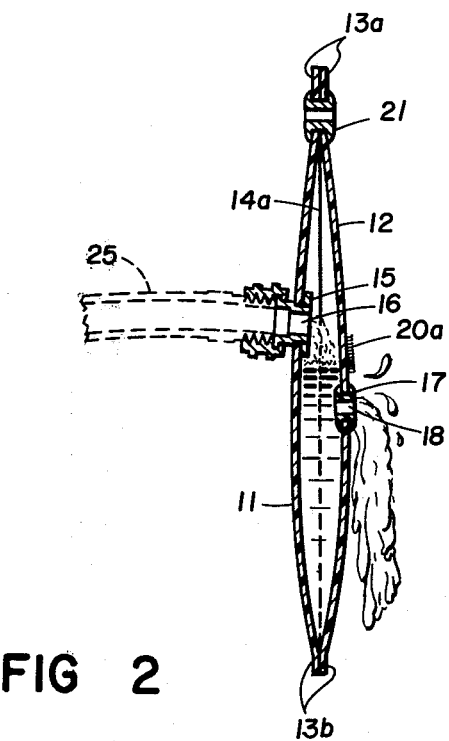
FIG. 2 is a sectional view taken along the line 2—2 of FIG. 1.

As shown in FIGS. 1 and 2, the essential part of the device consists of an elongated, envelope-shaped receptacle 10 formed from plastic Nylon. In any event, the receptacle 10 is fashioned from a pair of congruent panels 11 and 12 of the material having parallel opposite side edges 13a and 13b of arcuate shape and opposite end edges 14a and 14b. The corresponding edges 13 and 14 of the panels 11 and 12 are secured together by a solvent based adhesive and then heat sealed in order for the receptacle 10 to contain a liquid such as water, the sealing along the edge 13a being fairly extensive in area for reasons which will momentarily appear. Midway between its end edges 14 and somewhat biased toward its side edge 13 the panel 11 is apertured and fitted with a female hose coupling 15 to provide a liquid inlet 16. The opposite panel 12 is also apertured and fitted with grommets 17 spaced longitudinally of the panel 12 between its end edges 14 and somewhat biased toward its side edge 13b in order to provide a swath of liquid outlets 18 laterally across the device. The inlet 16 is therefore somewhat above the level of the outlets 18 when the device is in the position shown in FIG. 2.

In order to attach the device to and support it upon the animal, two lengths of Velcro material are employed plus an adjustable strap or straps. The hook and pile portions 20a and 20b of the Velcro are secured to the outer faces of the panels 11 and 12 and extend longitudinally thereof from the respective end edges 14a and 14b as shown in FIGS. 1 and 2. The sealed area along the side edge 13a is apertured and fitted with grommets 21 through which pass ties 22 adjustably secured at 23 to the respective ends of a strap 24 (see FIGS. 3 and 4).

Figure 3:
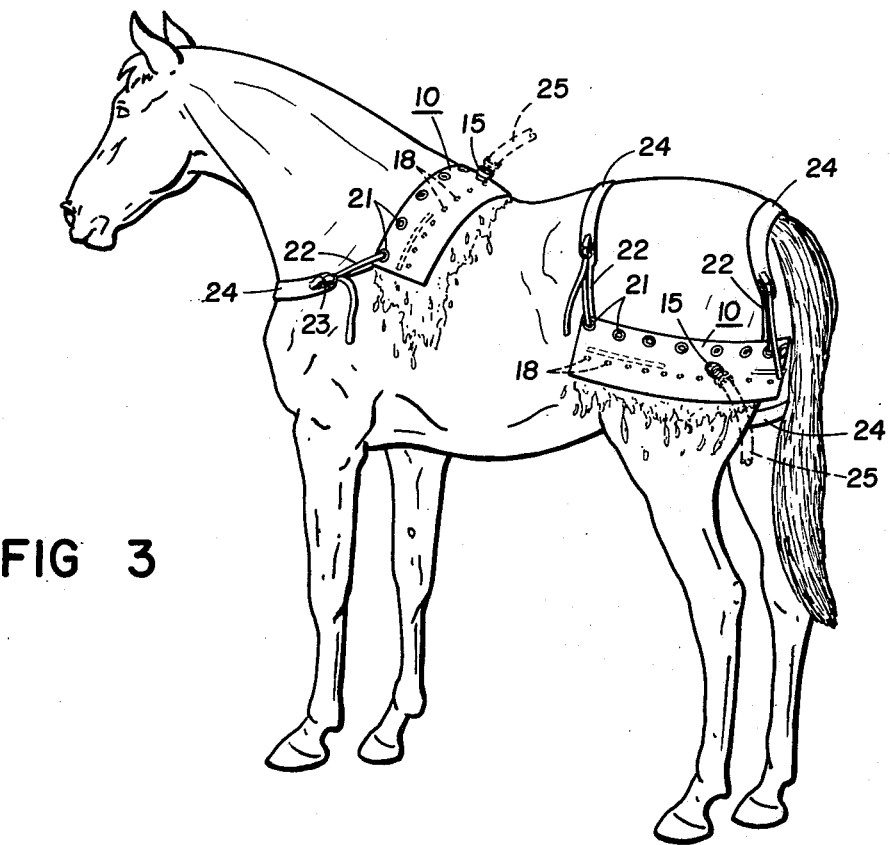
FIG. 3 illustrates a pair of the devices attached to a horse for treatment of upper body portions.
Figure 4:
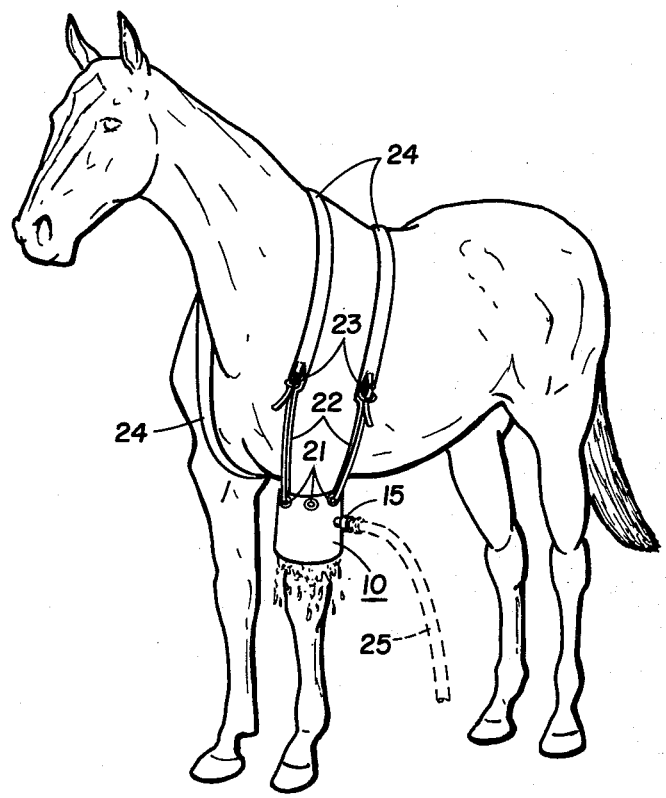
FIG. 4 illustrates the manner in which the device is used to treat a leg.

In FIG. 3 a pair of the devices are laid across the withers and thigh of the animal and supported in position by the straps 24 with the panels 11 and thus the outlets 18 facing and just above the area to be treated on the animal. Hoses, as indicated at 25, are then attached to the couplings 15. Water thus fills the receptacle 10 and cascades, as shown in FIGS. 2 and 3, from the outlets 18 against and down over the affected areas. Similar arrangements can be made to treat the loins, croup, hip, etc. When treating a leg, as shown in FIG. 4, the device is wrapped around the leg just above the affected area and secured thereabout by the Velcro strips 20, as well as being supported by the strap 24 over the body of the animal.

Though the present invention has been described in terms of a particular embodiment, being the best mode known of carrying out the invention, it is not limited to that embodiment alone. Instead, the following claims are to be read as encompassing all adaptations and modifications of the invention falling within its spirit and scope.

I claim:

1. Apparatus for treatment of swollen surface areas on larger animals such as horses comprising: an envelope-like receptacle effective to contain a liquid, the receptacle including first and second elongated panels of flexible sheet material forming oppositely facing sidewalls, each of the panels having a pair of opposite side edges and a pair of opposite end edges forming side and end edges of the receptacle, the panels being sealingly secured to each other along their corresponding edges in face to face relation; liquid inlet means for supplying liquid to the receptacle, the liquid inlet means being disposed in a first of the panels between said side edges and intermediate said end edges; a plurality of liquid outlet means for allowing liquid in the receptacle to flow therefrom, the liquid outlet means being disposed in a second of the panels longitudinally therealong between said end edges and intermediate said side edges; and means for applying the receptacle about or upon a portion of the anatomy of the animal with said second panel in facing relationship to the surface area to be treated effective to allow the outlet means to discharge liquid thereupon, the applying means including attaching means disposed adjacent said panel end edges and connectable together for attaching the receptacle about an animal's leg and suspending means disposed adjacent one of said panel side edges for suspending the receptacle from other portions of an animal's body either in conjunction with or independently of the attaching means.

2. The apparatus of claim 1 wherein the liquid inlet means is disposed between the liquid outlet means and said one of the panel side edges.

3. The apparatus of claim 2 wherein the attaching means includes complementary strips of Velcro material respectively disposed on the outer faces of the two panels, one of said strips extending longitudinally of said first panel from one of said end edges and the other of said strips extending longitudinally of said second panel from the other of said end edges.

4. The apparatus of claim 4 wherein the suspending means includes a plurality of apertures through both the two panels spaced longitudinally therealong between said end edges, and adjustable strap means securable to selected ones of the apertures.

* * * * *